United States Patent [19]

Reese

[11] Patent Number: 4,892,526

[45] Date of Patent: Jan. 9, 1989

[54] SURGICAL IRRIGATION APPARATUS

[76] Inventor: H. William Reese, 3214 S. River Rd., Tempe, Ariz. 85282

[21] Appl. No.: 234,029

[22] Filed: Aug. 18, 1988

[51] Int. Cl.$^4$ .............................................. A61M 7/00
[52] U.S. Cl. ..................................... 604/290; 604/310
[58] Field of Search ................ 604/73, 181, 183, 310, 604/311, 411, 412, 289, 290; 401/149, 150

[56] References Cited

U.S. PATENT DOCUMENTS

| 3,342,179 | 9/1967 | Ellmann | 604/412 |
| 3,930,761 | 1/1976 | Barraclough | 604/214 |
| 4,350,158 | 9/1982 | Hudson | 604/310 |
| 4,576,602 | 3/1986 | Levin et al. | 604/415 |

Primary Examiner—Stephen C. Pellegrino
Attorney, Agent, or Firm—Harry M. Weiss

[57] ABSTRACT

An surgical irrigation apparatus consisting of a container for a fluid suitable for irrigating tissue during surgical procedures, a conduit leading from the container and an adjustable pump spray nozzle attached to an opposing end of the conduit to permit an adjustable spray of fluid therefrom.

1 Claim, 1 Drawing Sheet

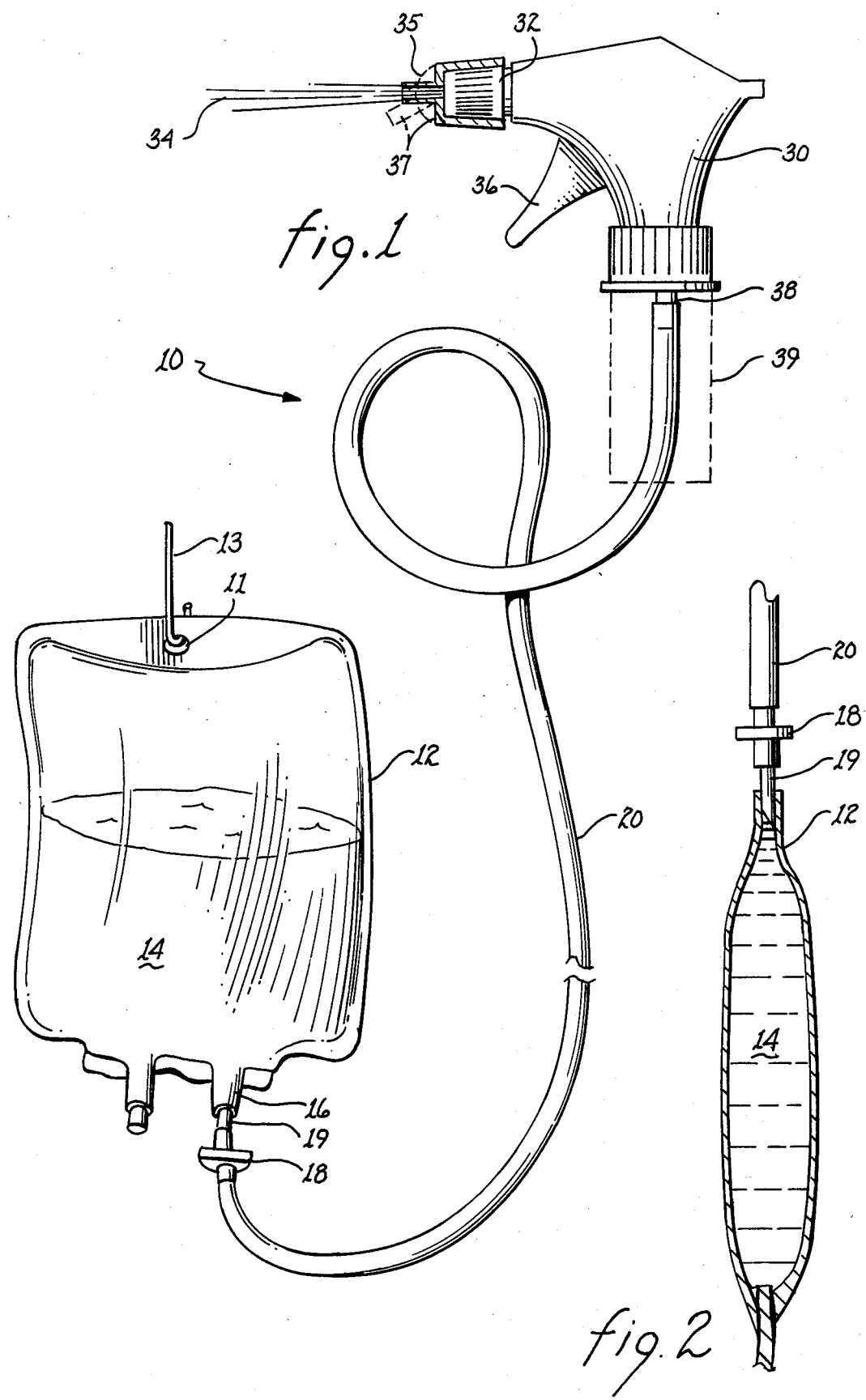

SURGICAL IRRIGATION APPARATUS

BACKGROUND OF THE INVENTION

The present invention relates generally to a surgical irrigation apparatus for irrigating tissue during surgical procedures. More particularly, the present invention relates to an apparatus consisting of a container for a fluid suitable for irrigating tissue during surgical procedures, a conduit leading from the container and an adjustable spray nozzle atttached to an opposing end of the conduit to permit an adjustable spray of fluid therefrom.

In the past surgical irrigation has been accomplished by flooding the exposed tissue area with an irrigation fluid and suctioning the fluid to clear the exposed tissue area. Thissue irrigation during surgical procedures is necessary to moisturize the exposed tissue to prevent tissue dehydration necrosis. Thus, it is necessary to periodically moisten the exposed tissue during surgery. Those persons skilled in the medical devices art have been unable to provide an irrigation fluid onto the exposed tissue area. Examplary of medical fluid dispensing devices are those disclosed in U.S. Pat. No. 4,108,178 issued Aug. 22, 1978 to Frank A. Betush entitled "Pinch Valve Syringe"; U.S. Pat. No. 3,254,646 issued June 7, 1966 to M. Staunt et al entitled "Dental Syringes"; U.S. Pat. No. 2,984,452 issued May 16, 1961 to W. J. Hooper entitled "Syringe"; and U.S. Pat. No. 2,757,667 issued Aug. 7, 1956 to F. E. Bronk entitled "Liquid Syringe."

In each of these exemplary prior art patents there is provided a syringe device for dispensing a pressurized jet of air and/or fluid from an air and/or fluid source. Typically, in each of these exemplary patents flow control is obtained byproviding a pinch valve to inhibit the flow of air and/or fluid through a conduit in the syringe. In surgical practices, it has been found that the pressurized fluid jet emitted from devices exemplified by the prior art devices is unsuitable for irrigation of surgically exposed tissue. The fluid jet emitted by the prior art devices tends to over-irrigate the exposed area and subject the exposed tissue to potentially damaging forces upon impact of the fluid with the tissue.

Accordingly, it has been found desirable to provide a manually controlled pump apparatus capable of dispensing controlled quantities of irrigation fluid in a spray form. A manually actuated syringe pump is disclosed in U.S. Pat. No. 4,204,539 issued on May 27, 1980 to Mathews Van Brugge entitled "Pumps and Syringes." The Van Brugge patent discloses a piston action pump/syringe for use in veterinary work for dispensing metered doses of liquids or pastes. The teaching of this patent addresses a mechanical configuration consisting of opposing one-way valves, one for pumping a metered dose of a liquid out of a central body and another for permitting ingress of a liquid or paste from a supply. The Van Brugge device ejects a jet of fluid with each depression of the pump, which is unsuitable for surgical irrigation purposes. While Van Brugge discloses one type of manually operated pump which may be used as a component of the present invention, that patent falls far short of disclosing the combined features taught by the present invention.

Thus, there is a need for a surgical irrigation apparatus which may be used to maintain moisturization of exposed tissue during surgical procedures without the need for flooding the exposed tissue.

SUMMARY OF THE INVENTION

Accordingly, it is an object of the present invention to provide a surgical irrigation apparatus for spraying sufficient quantities irrigation fluid onto exposed tissue during surgical procedures.

It is another object of the present invention to provide a surgical irrigation apparatus which obviates the need to flood an exposed tissue area with irrigation fluid during surgical procedures.

It is a further object of the present invention to provide a surgical irrigation apparatus having a manually actuated spray pump attached to an end of a fluid conduit. The fluid conduit is, in turn, connected at another end thereof to an container for the irrigation fluid, capable of being suspended in an inverted position to permit gravity flow of the irrigation fluid into the fluid conduit.

It is still a further object of the present invention to provide a surgical irrigation apparatus whereint eh fluid container is an intravenous bag or intravenous bottle to which the fluid conduit may be inserted with appropriate puncture fittings.

These and other objects, features and advantages of the present invention will become more apparent to those skilled in the art from the following more detailed description of the present invention with reference to the accompanying Figures in which like features are designated by like reference numerals.

BRIEF DESCRIPTION OF THE DRAWINGS

FIG. 1 is a side elevational view of a surgical irrigation apparatus in accordance with the present invention.

FIG. 2 is a side elevational cross-sectional view taken along line 2—2 of FIG. 1.

DETAILED DESCRIPTION OF THE PREFERRED EMBODIMENT

In accordance with the preferred embodiment of the present invention, and with particular reference to the accompanying Figures, there is provided a surgical irrigation apparatus 10 for applying an irrigation fluid to exposed tissue during surgical procedures. Surgical irrigation apparatus 10 consists of a container 12 capable of being suspended in an inverted position by a hanging means 13 connected to securing means 11 in the container 12. It is preferable, according to a preferred embodiment of the present invention, that container 12 consist of a plastic intravenous bag or bottle. Hanging means 13 will consist of any currently known intravenous stand having a hook, loop or other means for suspending the container 12 in an inverted position by engaging the securing means 11 in the container 12. Securing means 11 will consist, in the case of a plastic intravenous bag 12 of an aperture in an outer sealed seam of the intravenous bag 12, or, in the case of an intravenous bottle, may consist of a loop secured to the bottle.

A fluid outlet 16 is attached to container 12 and is in fluid flow communication with an interior evacuable chamber within container 12. When container 12 is filled with an irrigation fluid 14, irrigation fluid 14 substantially fills the interior evacuable chamber of container 12. It will be understood, by those skilled int eh relevant art, that irrigation fluid 14 may consist of any appropriate medical grade irrigation fluid, such as a 5% dextrose 0.9% sodium chloride in water solution. A fluid conduit 20, preferably any suitable medical-grade tubing, is connected at one end to the fluid outlet 16 of container 12. A second end of fluid conduit 20 is attached to a manually actuated pump spray nozzle apparatus 30. The pump spray nozzle apparatud 30 consists minimally of a coupling 38 for coupling the pump spray nozzle apparatus 30 to the second end of fluid conduit 20, a pump trigger 36 and an adjustable spray nozzle 32 for emitting a spray or mist 34 of irrigation fluid 14. Pump spray nozzle apparatud 30 is generally of the type having a trigger-actuated piston reciprocally disposed within a mainbody. The reciprocal motion of the piston within the main body creates opposing vacuum and pressure forces which draw fluid into the main body and emit fluid out of the main body, respectively. It is crucial that pump spray nozzle apparatus 30 be made of a medical-grade material, such as plastic, so that it may be repeatedly sterilized.

Fluid conduit 20 is preferably connected to fluid outlet 16 by a coupling having a hollow lance 19 protruding from a main body portion 18 of the lance coupling. As is well known in the pertinent art, intravenous bags have a puncturable covering which seals fluid outlet 16. To access the fluid 14 within the intravenous bag 16, the puncturable covering must be pierced by a coupling which permits flud flow outwardly from the interior evacuable chamber of the intravenous bag 12 and into fluid conduit.

In operation, the container 12 is suspended in an inverted position from an intravenous stand having hanging means 13. Normal gravitational forces cause the irrigation fluid 14 contained within the inner evacuable chamber of container 12 to flow outwardly from container 12, exiting container 12 from fluid outlet 16 and passing into fluid conduit 20. Upon filling fluid conduit 20, the irrigation fluid 14 is dispensed as spray 34 by the pumping action imparted by depressing pump trigger 36 thereby providing a motivating force moving irrigation fluid 14 from fluid conduit 20 into and through spray nozzle 30. Those skilled in the relevant art will recognize, however, that it is not essential or necessary that the container 12 be suspended in an inverted position due to the vacuum forces generated by the pumping action of the spray pump 30 will motivate a fluid flow irrespective of the position of container 12.

It will be appreciated, by those skilled in the art, that inversion of container 12 enables gravitational force to act as a fluid flow motivator through fluid conduit 20. By eliminating the need for a pressurized source of fluid, the disadvantages of fluid jet syringes disclosed by the prior art are alleviated. Utilization of gravity as the motivating fluid flow force permits theejection of a substantially non-pressurized spray 34. In this manner, spray 34 is emitted from spray nozzle 30 in only sufficient amounts to moisturize the surgically exposed tissue area. Thus, the present invention accomplishes its object of moisturizing surgically exposed tissue without flooding the area or increasing the risk of tissue damage due to the pressure of a fluid jet in the prior art devices.

Finally, it is preferable, though not essential, to provide a directional adapter 37 having either a straight, curved or angled spout which facilitates fine control voer positioning of the spray in the tissue to be irrigated. Further, it is desirable to employ a closure cap 35 which frictionally engages adjustable spray nozzle 32. Closure cap 35 permits multiple uses of the surgical irrigation apparatus 10 while maintaining sterile irrigation fluid.

Finally, to facilitate ease of handling and use, a handle 39 may be employed and attached to a coupling on the spray pump 30 and the handle 39.

While the invention has been particularly described and illustrated with reference to the preferred embodiments thereof, it is not intended that the invention be strictly limited to these embodiments. Those having ordinary skill in the art will recognize that variations and modifications differing from these embodiments, but falling within the spirit and scope of the invention, are possible. Other materials or configurations, for example, are contemplated by the present invention. All such variations and modifications as fall within the appended claims are therefore considered within the scope of the invention.

I claim:

1. A method, for providing sufficient quantities of irrigation fluid onto exposed tissue during surgical procedures, comprising the following:
   providing a plastic intravenous bag having a suitable fluid located within an inner evacuable chamber, a puncturable and sealable outlet opening, and a means attached to said bag for holding the bag in any desired elevated position;
   drawing the fluid from the intravenous bag through a fluid conduit made of flexible tubing, said conduit having a hollow lance coupling device for insertion into said outlet opening of said intravenous bag;
   drawing the fluid from said intravenous bag into said conduit to pump spray means which emits a spray of the fluid; and
   providng a multi-directional adapter at the outlet of said pump spray means to selectively direct the spray of the fluid in various directions while maintaining the pump spray means in one position.

* * * * *